United States Patent

Moguilewsky et al.

Patent Number: 5,006,518
Date of Patent: Apr. 9, 1991

[54] NOVEL 17β-HYDROXY-19-NOR-STEROIDS

[75] Inventors: Martine Moguilewsky, Paris; Lucien Nedelec, Le Raincy; Francois Nique, Pavillons-Sous-Bois; Daniel Philibert, La Varenne Saint-Hilaire, all of France

[73] Assignee: Roussel Uclaf, Paris, France

[21] Appl. No.: 292,475

[22] Filed: Dec. 30, 1988

[30] Foreign Application Priority Data

Dec. 30, 1987 [FR] France .................. 87 18376

[51] Int. Cl.$^5$ ............................. A61K 31/56
[52] U.S. Cl. .................. 514/179; 552/553; 552/554
[58] Field of Search .......... 514/179; 260/397.45

[56] References Cited

U.S. PATENT DOCUMENTS

| 4,233,296 | 11/1980 | Teutsch et al. | 260/397.45 |
|---|---|---|---|
| 4,386,085 | 5/1983 | Teutsch et al. | 514/179 |
| 4,447,424 | 5/1984 | Teutsch et al. | 260/397.45 |
| 4,519,946 | 5/1985 | Teutsch et al. | 260/397.45 |
| 4,536,401 | 8/1985 | Neef et al. | 260/397.45 |
| 4,547,493 | 10/1985 | Teutsch et al. | 260/397.45 |
| 4,609,651 | 9/1986 | Rohde et al. | 260/397.45 |
| 4,634,696 | 1/1987 | Teutsch et al. | 514/179 |
| 4,661,295 | 4/1987 | Jouquey et al. | 260/397.45 |
| 4,774,236 | 9/1988 | Cook et al. | 260/397.45 |
| 4,780,461 | 10/1988 | Neef et al. | 260/397.45 |
| 4,814,327 | 3/1989 | Ottow et al. | 514/179 |
| 4,829,060 | 5/1989 | Ottow et al. | 514/179 |

FOREIGN PATENT DOCUMENTS

| 0057115 | 8/1982 | European Pat. Off. | 514/179 |
|---|---|---|---|
| 0147361 | 7/1985 | European Pat. Off. | 260/397.45 |
| 0192598 | 8/1986 | European Pat. Off. | 514/179 |
| 3619413 | 12/1987 | Fed. Rep. of Germany | 260/397.45 |
| 2566779 | 1/1986 | France . | |

OTHER PUBLICATIONS

Structure of 11β-[4-(dimethylamino)phenyl]-17β-hydroxy-17α-(2-propenyl)estra-4,9-dien-3-one, Van Geerestein et al., Chemical Absts, vol. 106: 129694r.

Primary Examiner—H. M. Sneed
Assistant Examiner—James Saba
Attorney, Agent, or Firm—Biermand and Muserlian

[57] ABSTRACT

Novel 19-nor steroids of the formula

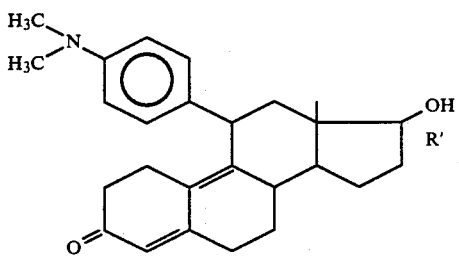

wherein R' is selected from the group consisting of propyl, propenyl, iodoethenyl, iodoethynyl or —C≡C—CH$_2$—Hal$_1$, Hal$_1$ is selected from the group consisting of fluorine, chlorine and bromine and their non-toxic, pharmaceutically acceptable acid addition salts having a remarkable antiglucocorticoid and antiprogestomimetic activity.

23 Claims, No Drawings

NOVEL 17β-HYDROXY-19-NOR-STEROIDS

STATE OF THE ART

Relevant prior art includes U.S. Pat. Nos. 4,233,296; 4,447,424; 4,519,946 and 4,634,695.

OBJECTS OF THE INVENTION

It is an object of the invention to provide the novel compounds of formula I and their non-toxic, pharmaceutically acceptable acid addition salts and a process for their preparation.

It is another object of the invention to provide antiglucocorticoid and antiprogestomimetic compositions and a method of inducing antiglucocorticoidal and antiprogestomimetic activity in warm-blooded animals.

These and other objects and advantages of the invention will become obvious from the following detailed description.

THE INVENTION

The novel compounds of the invention are selected from the group consisting of 19-nor steroids of the formula

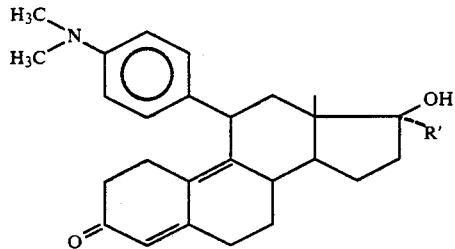

wherein R' is selected from the group consisting of propyl, propenyl, iodoethenyl, iodoethynyl or —C≡C—CH$_2$—Hal$_1$, Hal$_1$ is selected from the group consisting of fluorine, chlorine and bromine and their non-toxic, pharmaceutically acceptable acid addition salts.

Preferably, when R' is iodoethenyl, the double bond has E or Z geometry and when R' is propenyl, the double bond has Z geometry.

Specific preferred compounds of the invention are 17α-(3-chloro-1-propynyl)-11β-[4-(dimethylamino)-phenyl]-Δ$^{4,9}$-estradien-17β-ol-3-one, 11β-[4-(dimethylamino)-phenyl]-17α-(3-fluoro-1-propynyl)-Δ$^{4,9}$-estradien-17β-ol-3-one, 11β-[4-(dimethylamino)-phenyl]-21-iodo-19-nor-17α-Δ$^{4,9}$-pregnadien-20-yn-17β-ol-3-one, (E) 11β-[4-(dimethylamino)-phenyl]-21-iodo-19-nor-17α-Δ$^{4,9,20}$-pregnatrien-17β-ol-3-one, (Z) 11β-[4-(dimethylamino)-phenyl]-21-iodo-19-nor-17α-Δ$^{4,9,20}$-pregnatrien-17β-ol-3-one, 11β-[4-(dimethylamino)-phenyl]-17α-[(Z)-1-propenyl]-Δ$^{4,9}$-estradien-17β-ol-3-one, 11β-[4-(dimethylamino)phenyl)]-17α-propyl-Δ$^{4,9}$-estradien-17β-ol-3-one and 17α-(3-bromo-1-propynyl)-11β-[4-(dimethylamino)-phenyl]-Δ$^{4,9}$-estradien-17β-ol-3-one and their non-toxic, pharmaceutically acceptable acid addition salts.

Among the especially preferred compounds of the invention are in particular: 11β-[4-(dimethylamino)-phenyl]-17α-(3-fluoro-1-propynyl)-Δ$^{4,9}$-estradien-17β-ol-3-one, (Z) 11β-[4-(dimethylamino)-phenyl]-21-iodo-19-nor-17α-Δ$^{4,9,20}$-pregnatrien-17β-ol-3-one and 11β-[4-(dimethylamino)-phenyl]-17α-[(Z)-1-propenyl]-Δ$^{4,9}$-estradien-17β-ol-3-one and their non-toxic, pharmaceutically acceptable acid addition salts.

The process of the invention for the preparation of a compound of the formula

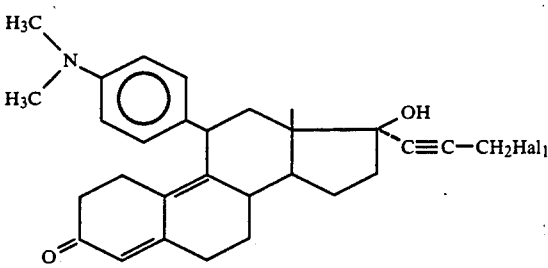

wherein Hal$_1$ has the above definition comprises reacting a compound of the formula

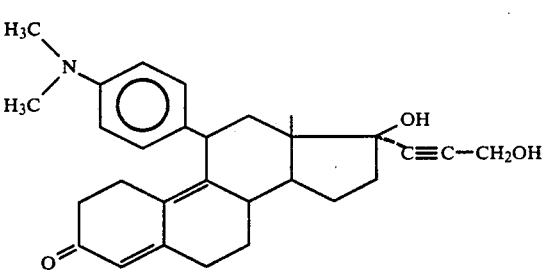

with a bromination or chlorination agent such as triphenylphosphine reacted with carbon tetrabromide or carbon tetrachloride in the presence of a solvent such as tetrahydrofuran or methylene chloride to obtain the compound of formula I$_{2A}$ wherein Hal$_1$ is chlorine or bromine and optionally reacting the latter with a fluorine exchange agent such as cesium fluoride or potassium fluoride in the presence of 18 crown 6 ether in acetonitrile.

The process for the preparation of compounds of the formula

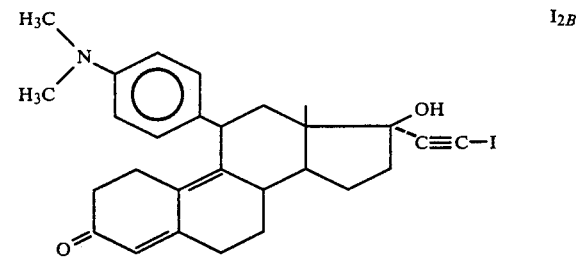

wherein the double bond has E or Z geometry comprises reacting a compound of the formula

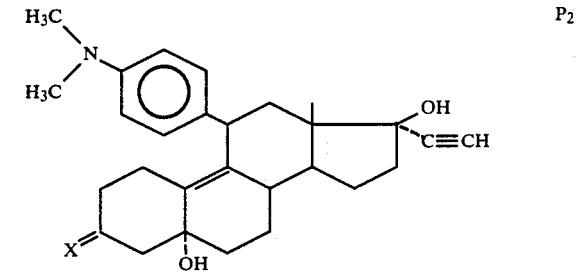

wherein k is a protected ketone such as ethylenedioxy with a reducing agent such as tributyltin hydride in the presence of azoisobutyronitrile to obtain an E bond or in a polar aprotic solvent such as hexamethylphosphotriamide to obtain a Z bond, reacting the latter with an iodization agent such as N-iodosuccinimide and then with a hydrolyzing agent to obtain the compound of formula $I_{2B}$ with the double bond having E or Z geometry.

The process of the invention for the preparation of a compound of the formula

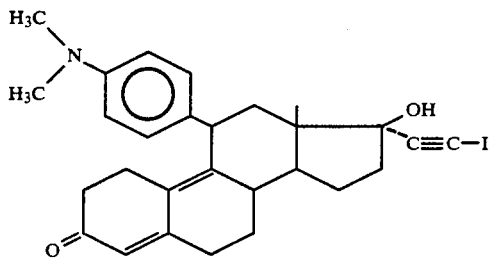

$I_{2C}$ comprises reacting a compound of the formula

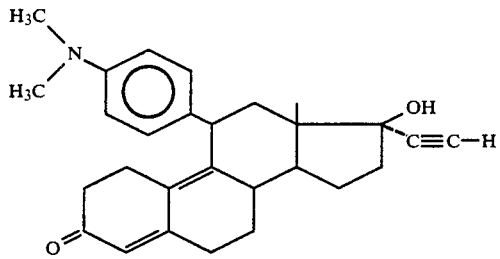

$P_3$ with an iodization agent such as N-iodo-succinimide in the presence of a silver salt such as silver carbonate or silver nitrate to obtain a compound of formula $I_{2C}$.

The process of the invention for the preparation of a compound of the formula

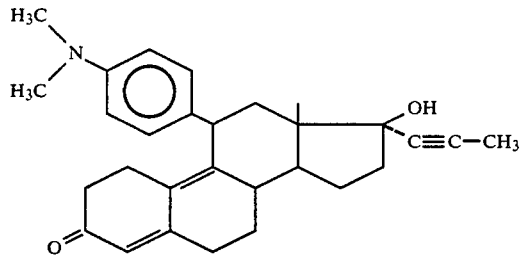

$I_{2D}$ wherein the dotted line is a single or double bond Z comprises reacting a compound of the formula

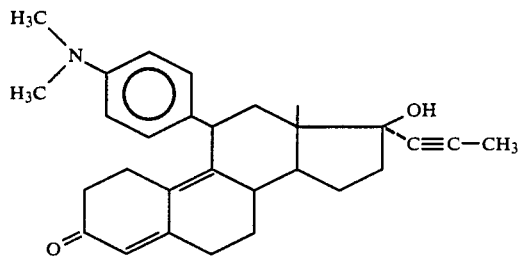

$P_4$ with hydrogen in the presence of a catalyst such as palladized barium sulfate poisoned with an amine such as pyridine or triethylamine to obtain a mixture of predominately a compound of the formula $I_{2D}$ wherein the dotted line is a second bond and Z geometry and a minor amount wherein the dotted line is a single bond.

Compound $P_1$ is described in French Pat. No. 2,566,779 and compounds $P_2$ and $P_3$ are described in European Pat. No. 0,057,115. Compound $P_4$ is described in French Pat. No. 2,497,807. The compounds of formula I fall within the scope of the broad formula of European Pat. No. 0,057,115 but are not described therein.

Examples of suitable salts for the preparation of the non-toxic, pharmaceutically acceptable acid addition salts are inorganic acids such as hydrochloric acid, hydrobromic acid, sulfuric acid, phosphoric acid and nitric acid and organic acids such as formic acid, acetic acid, propionic acid, fumaric acid, maleic acid, benzoic acid, aspartic acid, glycolic acid, succinic acid, alkane sulfonic acids such as methane sulfonic acid, ethane sulfonic acid and aryl sulfonic acids such as benzene sulfonic acid.

The novel antiglucocorticoid and antiprogestomimetic compositions of the invention are comprised of an effective amount of at least one compound of formula I and their non-toxic, pharmaceutically acceptable acid addition salts and an inert pharmaceutical carrier or excipient. The compositions may be in the form of tablets, dragees, gelules, granules, suppositories, ointments, creams, gels and injectable solutions or suspensions.

Examples of suitable excipients are talc, arabic gum, lactose, starch, magnesium stearate, cocoa butter, aqueous and non-aqueous vehicles, fatty substances of animal or vegetable origin, paraffinic derivatives, glycols, various wetting agents, surfactants and emulsifiers and preservatives.

In addition to their antiglucocorticoid and antiprogestomimetic activity, the compositions also possess androgen or antiandrogenic properties. Because of their antiglucocorticoid activity, the compositions are useful to counteract the side effects of glucocorticoids and are also useful to treat conditions caused by hypersecretion of glucocorticoid and especially against ageing in general and more particularly against hypertension, atherosclerosis, osteoporosis, diabetes, obesity as well as depression of immunity and insomnia. The compositions due to their antiprogestomimetic properties are useful as original contraceptives. They can also be used against hormonal disturbances and, furthermore they may present an interest in the treatment of hormone-dependent cancers.

The compositions possess antiprogestomimetic properties and can also be used in veterinary medicine as abortifacients and have particular use with female cats and dogs. The preferred veterinary medicaments contain 11$\beta$-[4-dimethylaminophenyl]-17$\alpha$-[(Z)-1-propenyl]-$\Delta^{4,9}$-estradien-17$\beta$-ol-3-one.

The novel method of the invention for inducing antiglucocorticoid and antiprogestomimetic activity in warm-blooded animals, including humans, comprises administering to warm-blooded animals an effective amount of at least one compound of Formula I and their non-toxic, pharmaceutically acceptable acid addition salts. The usual daily dosage is 0.13 to 13.33 mg/kg depending on the method of administration, the specific compound and the condition being treated. The compounds may be administered orally, rectally, parenterally or topically.

When used as abortifacients for female cats and dogs, the compounds may be administered with 1 to 3 injections per day at 3 to 5 mg/kg. For example, the compound of Product A of Example 6 may be administered at 5 mg/kg injections at 24 hour intervals for a female dog. For this use, the preferred compound is 11β-(4-dimethylamino-phenyl)-17α-[(ΔZ)-1-propenyl]-Δ$^{4,9}$-estradiene-17β-ol-3-one.

When the active compound to be administered is an antiglucocorticoid or an antiprogestomimetic, the preferred compounds are the compounds of Examples 2, 5 and 6 (Product A) and the usual oral dosages is 1.33 to 13.3 mg/kg.

In the following examples there are described several preferred embodiments to illustrate the invention. However, it should be understood that the invention is not intended to be limited to the specific embodiments.

EXAMPLE 1

17α-(3-chloro-1-propynyl)-11β/4-(dimethylamino)-phenylΔ$^{4,9}$-estradiene-17β-ol-3-one 800 mg of 11β-[4-(dimethylamino)-phenyl]-17α-(3-hydroxy-1-propynyl)-Δ$^{4,9}$-estradiene-17β-ol-3-one described in French Pat. No. 2,566,779 were dissolved in 8 ml of tetrahydrofuran and 8 ml of carbon tetrachloride and 950 mg of triphenylphosphine were added. The mixture was stirred at 90° C for 3 hours and a slightly insoluble product was filtered off. The filtrate was evaporated to dryness to obtain 1.40 g of crude product which was purified by chromatography on a silica column. Elution with a mixture of petroleum ether (b.p.: 40°-70° C.) and ethyl acetate (50/50) yielded 420 mg of pure expected product in the form of a crystalline solid melting at 238° C.

IR Spectrum (CHCl$_3$): OH 3600 cm$^{-1}$; C=O conjugated : 1655 cm$^{-1}$; C=C conjugated and aromatic; 1612/1562/1518 cm$^{-1}$.

EXAMPLE 2

11β-[4-(dimethylamino)-phenyl]-17α-(3-fluoro-1-propynyl)-Δ$^{4,9}$-estradien-17β-ol -3-one 313 mg of 17α-(3-chloro-1-propynyl)-11β-[4-(dimethylamino)-phenyl]-Δ$^{4,9}$-estradien-17β-ol-3-one were added with stirring to 10 mg of dry acetonitrile containing 600 ml of potassium fluoride and 600 mg of 18-crown 6 ether heated to 90° C. under an inert atmosphere. After 23 hours at reflux, the solvent was evaporated and the residue was dissolved in water and extracted by ethyl acetate. After washing with salted water and drying over magnesium sulfate, the organic phase was evaporated to dryness to obtain 322 mg of crude product which was purified by chromatography on silica column. Elution with a mixture of methylene chloride/ethyl acetate 90/10 yielded 79 mg of pure expected product which was crystallized from a mixture of methylene chloride and isopropyl ether to obtain 55 mg of the expected product melting at 234°-235° C.

IR Spectrum (CHCl$_3$): OH 3600 cm$^{-1}$; C=O conjugated: 1655 cm$^{-1}$; C=C conjugated+aromatic; 1612/1562/1568 cm$^{-1}$,

EXAMPLE 3

11β-[4-(dimethylamino)-phenyl]-21-iodo-19-nor-17α-Δ$^{4,9}$-pregnadien-20-yn-17β-ol-3-one 975 mg of 11β-[4-(dimethylamino)-phenyl]-19-nor-17α-Δ$^{4,9}$-pregnadien-20-ol-3-one were dissolved in 20 ml of acetone and 640 mg of silver carbonate then 450 mg of N-iodosuccinimide were added. The mixture was stirred for 4 hours and then was poured into a 10% aqueous solution of sodium thiosulfate and extracted with methylene chloride. The organic phase was washed with water, dried and evaporated to dryness to obtain 1.2 g of crude product which was chromatographed on silica. Elution at first with a cyclohexane-ethyl acetate mixture (6-4) yielded 390 mg of expected product and 760 mg of a mixture which was chromatographed on silica and eluted with a hexane-ether mixture (3-7) to obtain 530 mg of expected product. 920 mg of the product obtained were crystallized from ether to obtain 730 mg of product melting at 210° C. Another 79 mg of additional product was obtained from the mother liquors.

IR Spectrum (CHCl$_3$): OH 3598 cm$^{-1}$; C=C 2174 cm$^{-1}$; Dienone 1654 cm$^{-1}$; Aromatic 1612/1562/1518 cm$^{-1}$.

EXAMPLE 4

(E) 11β-[4-(dimethylamino)-phenyl]-21-iodo-19-nor-17α-Δ$^{4,9,20}$-pregnatrien-17β-ol-3-one Step A: (E) (1,2-ethanediyl) cyclic acetal of 11β-[4-(dimethylamino)-phenyl]-21-iodo-19-nor-17α-Δ$^{9,20}$-pregnadien-5α, 17β-diol-3-one (1) 1.5 g of (1,2-ethanediyl) cyclic acetal of 11β-[4-(dimethylamino)-phenyl]-19-nor-17α-Δ$^9$-pregnen-20-yn-5α, 17β-diol-3-one were dissolved in 30 ml of anhydrous tetrahydrofuran and 8 ml of tributyltin hydride and 300 mg of azoisobutyronitrile were added. The mixture was refluxed for 50 minutes and after concentrating under reduced pressure, the residual oil was diluted with methylene chloride and chromatographed on silica. Elution with a cyclohexane-ethyl acetate mixture (7-3) yielded 2.96 g of intermediary tributylstannyl-vinyl derivative.

(2) The latter was dissolved in 30 ml of anhydrous tetrahydrofuran, and 900 mg of N-iodosuccinimide were added. After 25 minutes of reaction, the mixture was poured into a 10% aqueous solution of sodium thiosulfate and extracted with methylene chloride. The organic phase was washed with water, dried and evaporated to dryness. The residue was taken into with isopropyl ether at reflux, then cooled with ice and separated to obtain 1.66 g of the expected product melting at 246° C.

IR Spectrum (CHCl$_3$): Free OH: 3600 cm$^{-1}$; OH in 5: 3500 cm$^{-1}$; Aromatics: 1613/1517 cm$^{-1}$.

Step B: (E) 11β-[4-(dimethylamino)-phenyl]-21-iodo-19-nor-17α-Δ$^{4,9,20}$-pregnatrien-17β-ol-3-one 1.66 g of the product of Step A were dissolved in 16 ml of methanol and 16 ml of 2N hydrochloric acid and the solution was stirred for 1 hour at ambient temperature. The mixture was poured into an aqueous solution of sodium bicarbonate, filtered and the precipitate was re-dissolved in methylene chloride. The organic phase was dried and evaporated to dryness under reduced pressure. The residue was chromatographed on silica and eluted with a cyclohexane-ethyl acetate mixture (7-3) to obtain 1.28 g of crude product. After dissolution in methylene chloride, concentration, then crystallization by the addition of ether, 1.125 g of the expected product melting at 236° C. after crystallization from ethanol were obtained.

IR Spectrum (CHCl₃): dienone C=O: 1654 cm⁻¹; C=C: 1612 cm⁻¹; Aromatic: 1518 cm⁻¹; OH: 3600 cm⁻¹.

EXAMPLE 5

(Z) 11β-[4-(dimethylamino)-phenyl]-21-iodo-19-nor-17α-Δ$^{4,9,20}$-pregnatrien-17β-ol-3-one Step A: (Z) (1,2-ethanediyl) cyclic acetal of 11β[4-(dimethylamino)-phenyl]-21-tributylstannyl-19-nor-17α-Δ$^{9,20}$-pregnadien-5α,17β-diol-3-one 477 mg of (1,2-ethanediyl) cyclic acetal of 11β-[4-(dimethylamino)-phenyl]-19-nor-17α-Δ$^9$-pregnen-20-yn-5α,17β-diol-3-one were dissolved in 5 ml of hexamethylphosphorotriamide and 2,6 ml of tributyltin hydride were added under an inert atmosphere. The mixture was heated to 70° C. for 25 hours, then cooled, diluted with water and extracted with ethyl acetate. The organic phase was washed with water, dried and concentrated to dryness. The residue was chromatographed on silica and eluted with a petroleum-ether (b.p: 40°-70° C.) /ether mixture (6-4) to obtain 214 g of isomer (E), 135 mg of the mixture of isomers (E) and (Z) and 346 mg of the expected isomer (Z).

Step B: (Z) 11β-[4-(dimethylamino)-phenyl]-21-iodo-19-nor-17α-Δ$^{4,9,20}$-pregnatrien-17β-ol-3-one 1.47 g of the isomer (Z) of Step A were dissolved in 30 ml of tetrahydrofuran and 520 mg of N-iodosuccinimide were added with stirring. After 30 minutes at ambient temperature, the mixture was poured into an aqueous solution of sodium thiosulfate and extracted with ethyl line dropped to dryness. 10 ml of methanol and 10 ml of 2N hydrochloric acid were added to the residue which stood for 1 hour. The mixture was then alkalized with a solution of sodium bicarbonate and extracted with methylene chloride. The organic phase was washed with water, dried, then concentrated to dryness to obtain 1.36 g of crude product. The residue was chromatographed on silica and eluted with a cyclohexane-ethyl acetate mixture to obtain 600 mg of the expected product melting at 178° C. after crystallization from ether.

IR Spectrum (CHCl₃): Region C=O: 1650 cm⁻¹; C=C: 1612 cm⁻¹; Aromatic: 1518 cm⁻¹; OH: 3590 cm⁻¹ and 3540 cm⁻¹.

EXAMPLE 6

(Z) 11β-[4-(dimethylamino)-phenyl]-17α-[(Z)1-propenyl]-Δ$^{4,9}$-estradien-17β-ol-3-one (Product A) and 11β-[4-(dimethylamino)-phenyl]-17α-propyl-Δ$^{4,9}$-estradien-17β-ol-3-one (Product B)

1 g of 11β-[4-(dimethylamino)-phenyl]-17α-(1-propynyl)-Δ$^{4,9}$-estradien-17β-ol-3-one were dissolved in 50 ml of ethanol and 1 ml of triethylamine and 75 mg of 10% palladium hydroxide on barium sulfate were added. The mixture was hydrogenated at ordinary temperature and it was stopped after the absorption of 55 ml of hydrogen. The catalyst was filtered off, the product was rinsed in ethanol and then the solvents were evaporated to obtain 1.076 g of crude product which was chromatographed on a silica column (eluant cyclohexane-ethyl acetate; 70-30). The following were obtained in succession: 92 mg of (Z) 11β-[4-(dimethylamino)-phenyl]-17α-[(Z)1-propenyl]-Δ$^{5(10)}$-estren-17β-ol-3-one (Rf: 0.40). 568 mg (Z) 11β-[4-(dimethylamino)-phenyl]-17α-[(Z)1-propenyl]-Δ$^{4,9}$-estradien-17β-ol-3-one (Rf: 0.27 Product A) and 59 mg of 11β-[4-dimethylaminophenyl]-17α-propyl-Δ$^{4,9}$-estradien-17β-ol-3-one (RF: 0.24) (Product B).

PHYSICOCHEMICAL CONSTANTS OF PRODUCT A

Analysis: C₂₉H₃₇NO₂; molecular weight=431.63 Calculated: C % 80.70; H % 8.64; N % 3.25. Found: C % 80.34; H % 8.7; N % 3.2.

IR Spectrum (CHCl₃): OH at 3608 cm⁻¹; C=O and C=C conjugated 1654/1612 cm⁻¹; aromatic 1580/1518 cm⁻¹.

UV Spectrum (Et OH); Max 258 nm=17,900; Max 303 nm=22,700; +HCL 0.1N max; 301 nm=21,300.

PHYSIOCHEMICAL CONSTANTS OF PRODUCT B

IR Spectrum (CHCl₃) OH at 3615 cm⁻¹ C=O/C=C conjugated 1654/1612 cm⁻¹; Aromatic 1560/1518 cm⁻¹.

EXAMPLE 7

17α-(3-bromo1-propynyl)-11β-[4-(dimethylamino)-phenyl]-Δ$^{4,9}$-estradien-17β-ol-3-one 600 mg of 11β-[4-(dimethylamino)-phenyl]-17α-(3-hydroxy-1-propynyl)-Δ$^{4,9}$-estradien-17β-ol-3-one were dissolved in 6 ml of methylene chloride with 491 mg of carbon tetrabromide and after the solution was cooled to −10° C., a solution of 531 mg of triphenylphosphine in 3 ml of methylene chloride was added dropwise. The mixture was stirred for 20 minutes at −10° C. and was placed on a silica column of 15 g of silica and eluted with a mixture of petroleum-ether (b.p. 40°-70° C.)/ethyl acetate 50/50 to obtain 384 g of pure expected product in solid crystalline form.

PHARMACEUTICAL COMPOSITIONS

Tablets were prepared containing 200 mg of the product of Example 6 (Product A) and sufficient quantity of excipient of talc, starch, magnesium stearate for a tablet weight of 350 mg.

VETERINARY COMPOSITIONS

An injectable solution was prepared containing 100 mg of the product of Example 6 (Product A), 0.3 ml of ethanol and peanut oil q.s.p. to 3 ml.

PHARMACOLOGICAL STUDY

I. Study of the activity of the products of the invention on the hormonal receptors:

A. Progesterone receptor in the uterus of a female rabbit:

Impuberal rabbits of approximately 1 kg received a cutaneous application of 25 g estradiol and 5 days after the treatment, the animals were killed. The uteruses were removed, weighed and homogenized at 0° C. with the help of a Potter Teflon glass in a buffer solution (Tris 10 mM, saccharose 0.25M.

HCl pH 7.4) (1 g of tissue for 50 ml of TS). The homogenate was then ultra-centrifuged (105,000 g×90 min) at 0° C. The supernatant aliquotes thus obtained were incubated at 0° C. for a time t, with a constant concentration (T) of Product R tritiated (17,21-dimethyl-19-nor-Δ4,9-pregnadien-3,20-dione) in the presence of increasing concentrations (0–2,500. 10⁻⁹M) either of cold R, or of cold progesterone, or of the cold product to be tested. The concentration of bound tritiated R (B)

was then measured in each incubate by the absorption technique by dextran carbon.

B. Glucocorticoid receptor in the thymus of a rat:

Male Sprague-Dawley EOPS rats weighing 160 to 200 g underwent suprarenalectomies. 4 to 8 days after this removal, the animals were killed and the thymus were removed and homogenized at 0° C. in Tris 10 mM buffer, saccharose 0.25M, dithiothreitol 2 mM, HCl pH, 7, 4, in a Potter polytetrafluoroethylene-glass (1 g of tissue for 10 ml of TS). The homogenate was then ultracentrifuged (105,000 g×90 mn) at 0° C. Aliquotes of the supernatant thus obtained were incubated at 0° C. for a time (t) with a constant concentration (T) of dexamethasone tritiated in the presence of increasing concentrations (0–2,500. $10^9$M) either of cold dexamethasone or of cold product to be tested. The concentration of bound tritiated dexamethasone (B) was then measured in each incubate by the technique of adsorption on carbon dextran.

C. Calculation of the relative affinity of bonding:

The calculation of the relative affinity of bonding (RAB) was indentical for all the receptors.. The following 2 curves were traced: the percentage of the tritiated hormone in B as a function of the logarithm of the concentration of the cold product tested. The straight line of the equation $$I^{50} = \left( \frac{B}{T} \max + \frac{B}{T} \min. \right)/2 \text{ was determined.}$$

B max=Percentage of the tritiated bound hormone for an T incubation of this tritiated hormone at the concentration (T).

B min=Percentage of the tritiated bound hormone for an T incubation of this tritiated hormone at the concentration (T), in the presence of a great excess of cold hormone (2500. $10^{-9}$M).

The intersections of the straight line $I_{50}$ and the curves permit the evaluation of the concentrations of the reference cold hormone (CH) and of the cold product tested (CX) which inhibited by 50% of the bonding of the tritiated hormone on the receptor.

The relative affinity of the bonding (RAB) of the product tested is determined by the equation:

$$RAB = 100 \frac{(CH)}{(CX)}$$

The following results were obtained:

| Incubation time at 0° C. | Products of the examples | | | |
|---|---|---|---|---|
| | Progestrogen | | Glucocorticoid | |
| | 2H | 24H | 4H | 24H |
| 1 | 72 | 286 | 139 | 159 |
| 5 | 41 | 184 | 146 | 113 |
| 6 (Product A) | 96 | 491 | 147 | 115 |

ABORTIVE ACTIVITY IN THE FEMALE DOG

Preparation of the solution of the product to be studied 250 mg of the product to be studied were dissolved in 1 ml of methylene chloride and then 1 ml of this solution was diluted with sesame oil until 250 ml of the final solution was obtained.

The state of gestation of the from 16 months to 4 years old female dogs, is determined by echography and the duration of the gestation is noted which extends from 25 to 40 days.

The product to be studied is administered sub-cutaneously in solution corresponding to the preparation above in a 5 mg/kg dose and 2 injections are given at an interval of 24 hours.

A control echograph is carried out 3 to 10 days after the last injection.

3 days after the injection of the product of example 6 (Product A) an abortion was observed in 66% of the cases.

10 days after the injection of the product of example 6 (Product A) a complete abortion was observed in all the animals in the group.

ABORTIVE ACTIVITY IN THE FEMALE RABBIT 10 days after covering the female rabbits received a sub-cutaneous injection of the product to be studied in a solution corresponding to the preparation above, in a 4 mg/kg and 5 mg/kg dosage was effected and 10 days after the treatment, the animals were killed and the number of abortions which has taken place were noted at the autopsy. A complete abortion had taken place in all of the animals of the group with the product of Example 6 (Product A) administered in 4 mg/kg and 5 mg/kg dosage.

Various modifications of the products and method may be made without departing from the spirit of scope thereof and it is to be understood that the invention is intended to be limited only as defined in the appended claims.

What is claimed is:

1. A compound selected from the group consisting of 19-nor steroids of the formula

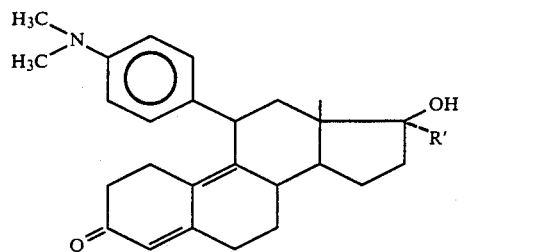

wherein R' is selected from the group consisting of propyl, prop-1-enyl, iodoethenyl, iodoethynyl or —C≡C—CH$_2$—Hal$_1$, Hal$_1$ is selected from the group consisting of fluorine, chlorine and bromine and their non-toxic, pharmaceutically acceptable acid addition salts.

2. A compound of claim 1 selected from the group consisting of 17α-(3-chloro-1-propynyl)-11β-[4-(dimethylamino)-phenyl]-Δ$^{4,9}$-estradien-17β-ol-3-one and its non-toxic, pharmaceutically acceptable acid addition salts.

3. A compound of claim 1 selected from the group consisting of 11β-[4-(dimethylamino)-phenyl]-17α-(3-fluoro-1-propynyl)-Δ$^{4,9}$-estradien-17β-ol-3-one and its non-toxic, pharmaceutically acceptable acid addition salts.

4. A compound of claim 1 selected from the group consisting of 11β-[4-(dimethylamino)-phenyl]-21-iodo-19-nor-17α-Δ$^{4,9}$-pregnadien-20-yn-17β-ol-3-one and its non-toxic, pharmaceuticaly acceptable acid addition salts.

5. A compound of claim 1 selected from the group consisting of (E) 11β-[4-(dimethylamino)-phenyl]21-iodo-19-nor-17α-Δ$^{4,9,20}$-pregnatrien-17β-ol-3-one and its non-toxic, pharmaceutically acceptable acid addition salts.

6. A compound of claim 1 selected from the group consisting of (Z) 11β-[4-(dimethylamino)-phenyl]21-iodo-19-nor-17α-Δ$^{4,9,20}$-pregnatrien-17β-ol-3-one and its non-toxic, pharmaceutically acceptable acid addition salts.

7. A compound of claim 1 selected from the group consisting of 11β-[4-(dimethylamino)-phenyl]-17α-[(Z)-1-propenyl]-Δ$^{4,9}$-estradien-17β-ol-3-one and its non-toxic, pharmaceutically acceptable acid addition salts.

8. A compound of claim 1 selected from the group consisting of 11β-[4-(dimethylamino)-phenyl]-17α-propyl-Δ$^{4,9}$-estradien-17β-ol-3-one and its non-toxic, pharmaceutically acceptable acid addition salts.

9. A compound of claim 1 selected from the group consisiting of 17α-(3-bromo-1-propynyl)-11-β[4-(dimethylamino)-phenyl]-Δ$^{4,9}$-estradien-17β-ol-3-one and its non-toxic, pharmaceutically acceptable acid addition salts.

10. An antiglucocorticoid composition comprising an antiglucocorticoidally effective amount of at least one compound of claim 1 and an inert pharmaceutical carrier.

11. A composition of claim 10 wherein the active compound is selected from the group consisting of 17α-(3-chloro-1-propynyl)-11β-[4-(dimethylamino)-phenyl]-Δ$^{4,9}$-estradien-17β-ol-3-one, 11β-[4-(dimethylamino)-phenyl]-17α-(3-fluoro-1-propynyl)-Δ$^{4,9}$-estradien-17β-ol-3-one, 11β-[4-(dimethylamino)-phenyl]-21-iodo-19-nor-17α-Δ$^{4,9}$-pregnadien-20-yn-17β-ol-3-one, (E) 11β-[4-(dimethylamino)-phenyl]-21-iodo-19-nor-17α-Δ$^{4,9,20}$-pregnatrien-17β-ol-3-one, (Z) 11β-[4-(dimethylamino)-phenyl]-21-iodo-19-nor-17α-Δ$^{4,9,20}$-pregnatrien-17β-ol-3-one, 11β-[4-(dimethylamino)-phenyl]-17α-[(Z)-1-propenyl]-Δ$^{4,9}$-estradien-17β-ol-3-one, 11β-[4-(dimethylamino)-phenyl)]-17α-propyl-Δ$^{4,9}$-estradien-17β-ol-3-one and 17α-(3-bromo-1-propynyl)-11β-[4-(dimethylamino)-phenyl]-Δ$^{4,9}$-estradien-17β-ol-3-one and its non-toxic, pharmaceutically acceptable acid addition salts.

12. A composition of claim 10 wherein the active compound is selected from the group consisting of 11β-[4-(dimethylamino)-phenyl]-17α-(3-fluoro-1-propynyl)-Δ$^{4,9}$-estradien-17β-ol-3-one, (Z) 11β-[4-(dimethylamino)-phenyl]-21-iodo-19-nor-17α-Δ$^{4,9,20}$-pregnatrien-17β-ol-3-one and 11β-[4-(dimethylamino)-phenyl]-17α-[(Z)-1-propenyl]-Δ$^{4,9}$-estradien-17β-ol-3-one and its non-toxic, pharmaceutically acceptable acid addition salts.

13. An abortifacient composition for animals comprising an abortifaciently effective amount of the compound of claim 1 and pharmaceutical carrier.

14. A composition of claim 13 comprising an effective amount of the compounds of claim 3 and 11.

15. A composition of claim 13 for animals comprising an effective amount of the compound of claim 12.

16. A method of inducing antiglucocorticoid activity in warm-blooded animals comprising administering to warm-blooded animals an antiglucocorticoidally effective amount of at least one compound of claim 1.

17. A method of claim 16 wherein the active compound is selected from the group consisting of 17α-(3-chloro-1-propynyl)-11β-[4-(dimethylamino)-phenyl]-Δ$^{4,9}$-estradien-17β-ol-3one, 11β-[4-(dimethylamino)-phenyl]-17α-(3-fluoro-1-propynyl)-Δ$^{4,9}$-estradien-17β-ol-3-one, 11β-[4-(dimethylamino)-phenyl]-21-iodo-19-nor-17α-Δ$^{4,9}$-pregnadien-20-yn-17β-ol-3-one, (E) 11β-[4-(dimethylamino)-phenyl]-21-iodo-19-nor-17α-Δ$^{4,9,20}$-pregnatrien-17β-ol-3-one, (Z) 11β-[4-(dimethylamino)-phenyl]-21-iodo-19-nor-17α-Δ$^{4,9,20}$-pregnatrien-17β-ol-3-one, 11β-[4-(dimethylamino)-phenyl]-17α-[(Z)-1-propenyl)-Δ$^{4,9}$-estradien-17β-ol-3-one, 11β-[4-(dimethylamino)-phenyl)]-17α-propyl-Δ$^{4,9}$-estradien-17β-ol-3-one and 17α-(3-bromo-1-propynyl)-11β-[4-(dimethylamino)-phenyl]-Δ$^{4,9}$-estradien-17β-ol-3-one and its non-toxic, pharmaceutically acceptable acid addition salts.

18. A method of claim 16 wherein the active compound is selected from the group consisting of 11β-[4-(dimethylamino)-phenyl]-17α-(3-fluoro-1-propynyl)-Δ$^{4,9}$-estradien-17β-ol-3-one, (Z) 11β-[4-(dimethylamino)-phenyl]-21-iodo-19-nor-17α-Δ$^{4,9,20}$-pregnatrien-17β-ol-3-one and 11β-[4-(dimethylamino)-phenyl]-17α-[(Z)-1-propenyl]-Δ$^{4,9}$-estradien-17β-ol-3-one and its non-toxic, pharmaceutically acceptable acid addition salts.

19. A method of inducing abortion in pregnant female warm-blooded animals comprising administering to pregnant fermale warm-blooded animals an abortion effective amount of the compound of claim 1.

20. A method of claim 19 comprising administering to pregnant female warm-blooded animals an abortion effective amount of the compound of claim 3 and 11.

21. A method of claim 19 comprising administering to pregnant female warm-blooded animals an abortion effective amount of the compound of claim 7.

22. An anti-progestomimetic composition comprising an anti-progestomimetically effective amount of at least one compound of claim 1 and an inert pharmaceutical carrier.

23. A method of inducing anti-progestomimetic activity in warm-blooded animals comprising administering to warm blooded animals an anti-progestomimetically effective amount of at least one compound of claim 1.

* * * * *